(12) United States Patent
Frater et al.

(10) Patent No.: US 6,569,411 B2
(45) Date of Patent: May 27, 2003

(54) SERINE CARBONATES

(75) Inventors: Georg Frater, Winterthur (CH); Denise Anderson, Zürich (CH); Frank Kumli, Niedererlinsbach (CH); Jens Wittenberg, Freiburg (DE); Virginia Streusand Goldman, Morris Plains, NJ (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 10/219,964

(22) Filed: Aug. 15, 2002

(65) Prior Publication Data

US 2003/0018055 A1 Jan. 23, 2003

Related U.S. Application Data

(62) Division of application No. 09/601,225, filed as application No. PCT/CH99/00585 on Dec. 7, 1999, now abandoned.

(51) Int. Cl.[7] .................. A61K 7/32; A61K 7/34; A61K 7/36; A61K 7/38
(52) U.S. Cl. .................. 424/65; 424/66; 424/68; 554/101; 554/107; 560/158; 560/159; 560/160; 562/561; 562/563
(58) Field of Search .................. 424/65, 66, 68; 554/101, 107; 560/159, 169, 158; 562/561, 563

(56) References Cited

U.S. PATENT DOCUMENTS

| | | | |
|---|---|---|---|
| 5,431,904 A | | 7/1995 | Laney .................. 424/65 |
| 5,514,671 A | * | 5/1996 | Lyson et al. .................. 514/104 |
| 5,925,339 A | | 7/1999 | Acuna et al. .................. 424/65 |

FOREIGN PATENT DOCUMENTS

| | | | |
|---|---|---|---|
| EP | 816322 | * | 1/1998 |
| EP | 1008587 | * | 6/2000 |
| WO | WO 91/11988 | | 8/1991 |
| WO | WO 92/19643 | | 11/1992 |

OTHER PUBLICATIONS

Frankel, M., et al., *J. Chem. Society*, 2735–37 (1952).
Oki, K., et al., *Bull. Chem. Soc. Japan*, 43(8), 2554–58, (1970).
Schnabel, V.E., et al., *Liebigs Ann. Chem.*, 743, 57–68, (1971).
Kiso, Y., et al., *Chem. Pharma. Bull.*, 36(12), 5024–27, (1988).
Loffet, A., et al., *Int. J. Peptide & Protein Res.*, 42, 346–51, (1993).
Dessolin, M., et al., *Tetrahedron Letters*, 36(32), 5471–44, (1995).
Baldwin, J.E., et al., *Tetrahedron Letters*, 37(21), 3761–64, (1996).
Atherton, E., et al., *J. Chem. Soc.*, 1, 2887–94, (1988).
Maruyama, K., et al. *J. Org. Chem.*, 57, 6143, (1992).
Shute, R. E., et al., *Synthesis*, (4), 346–49, (1987).
Skinner, C. G., et al., *J. Am. Chem. Soc.*, 78(11), 2412–14, (1994).
Pirrung, M.C., et al., *J. Org. Chem.*, 59(14), 3890–97, (1994).
Barton & Ollis, *Comp. Organic Chem.*, 2, 1074–78, (1979).
Barton & Ollis, *Comp. Organic Chem.*, 2, 871–907, (1979).
Barton & Ollis, *Comp. Organic Chem.*, 2, 1083–84, (1979).
Barton & Ollis, *Comp. Organic Chem.*, 2, 1070–1071, (1979).
Kabara, J.J., *Cosmet. Sci. Techno. Ser.*, 16, 181–208, (1997).

* cited by examiner

Primary Examiner—Sabiha Qazi
(74) *Attorney, Agent, or Firm*—Stephan P. Williams

(57) ABSTRACT

Serine carbonates of formula I are precursors for organoleptic compounds, masking agents and antimicrobial agents. Further they are alternative substrates for malodor producing enzymes. The symbols in formula I are defined in claim 1.

9 Claims, No Drawings

SERINE CARBONATES

This application is a division of Ser. No. 09/601,225 now abandoned which is a 371 of PCT/CH99/00585 filed on Dec. 7, 1999.

The present invention relates to serine carbonates and the use of serine carbonates as precursors for (a) organoleptic compounds, especially for fragrances, flavors and/or (b) masking agents, and/or (c) antimicrobial compounds and/or (d) alternative substrates for malodor producing enzymes.

A principal strategy currently employed in imparting odors to consumer products is the admixing of a fragrance, masking agent or antimicrobial compound directly into the product to be treated. There are, however, several drawbacks to this strategy. The fragrance material can, for example, be too volatile and/or too soluble, resulting in fragrance loss during manufacturing, storage and use. Many fragrance materials are also unstable over time. This again results in loss during storage.

In many consumer products it is desirable for the fragrance to be released slowly over time. Microencapsulation and inclusion complexes, especially with cyclodextrins, have been used to help decrease volatility, improve stability and provide slow-release properties. However, these methods are for a number of reasons often not successful. In addition, cyclodextrins can be too expensive.

In consumer products such as deodorants, the aim is to mask malodor or to block its production and optionally also to provide a pleasant fragrance. Deodorants are generally of three types: odor maskers, antiperspirants, and germicides. Despite the many disclosures in the art pertaining to deodorant compositions, current products are not sufficient to suppress odor in a significant proportion of the population, particularly during periods of stress. There remains a need for new deodorant compositions and methods which are effective, safe and economical.

Carbonate-derived fragrance precursors having mercapto or ether groups useful for laundry, deodorant and other applications are described in EP 816 322.

WO 91/11988 refers to alternative enzyme substrates as deodorants. The substrates are amino acids containing an 0-acyl or 0-thio group.

U.S. Pat. No. 5,431,904 relates to a deodorant composition comprising a compound which is capable of serving as an alternative substrate. Disclosed is a deodorant composition comprising O-acylated serine derivatives which compete with the naturally occurring malodor producing precursor. In a preferred embodiment, the O-acylated serine may generate organoleptic acids in the axilla concomitant with suppressing the malodor.

An object of the present invention is to provide new precursors for organoleptic and/or antimicrobial compounds and/or alternative substrates for malodor producing enzymes.

A further object of the invention is to provide such new precursors which are stable under usual transport and storage conditions. Optionally, the precursors of the present invention may release more than one active component.

It has now been found that serine carbonates of formula I

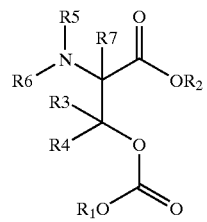

or a salt thereof
wherein
$R^1$ is the residue of an organoleptic alcohol, phenol or of the enol form of an organoleptic aldehyde or ketone of formula $R^1OH$, $R^2$ is hydrogen, metal, ammonium, straight or branched alkyl, alkenyl, alkinyl, cycloalkyl, cycloalkenyl, heterocycloalkyl, heterocycloalkenyl, aryl or heteroaryl, whereby all organic residues may contain heteroatoms and may carry substituents and if $R^2$ is hydrogen $R^1$ is not the residue of benzyl alcohol, $R^3$, $R^4$ and $R^7$ are independently hydrogen or lower alkyl and either $R^3$ and $R^4$ or $R^3$ and $R^7$ or $R^4$ and $R^7$ may form together a ring, $R^5$ and $R^6$ are independently hydrogen, straight or branched alkyl, alkenyl, alkinyl, cycloalkyl, cycloalkenyl, heterocycloalkyl, an aromatic or hetero aromatic residue, alkylcarbonyl, alkoxycarbonyl, arylcarbonyl, aryloxycarbonyl and $R^5$ and $R^6$ may together form a ring, whereby all organic residues may contain heteroatoms and may carry substituents, fulfill the aforementioned tasks and, hence, are useful for the aforementioned purposes.

The compounds of formula I are not limited to any particular stereoisomers, all possible stereoisomers (E/Z isomers, enantiomers, diastereomers) and all mixtures are thus included within the scope of the invention. Salts are also included in the general formula.

The compounds of formula I may be prepared as quaternary salts.

$R^2$, $R^5$ and/or $R^6$ may contain heteroatoms selected of from the group O, N, S, P and Si.

$R^2$, $R^5$ and/or $R^6$ may also carry one or more of the following substituents -halogen, -aryl, -heteroaryl, cycloalkyl, -cycloalkenyl, -heterocycloalkenyl, —OH, —OR, —NCOON=CR$_2$, —OCOON=CR$_2$, —COON=CR$_2$ —NO$_2$, —COR, —C(OR)$_2$R, —COOR, —CONR$_2$, OCOR, —OCOOR, OCONR$_2$, —NR$_2$, —SOR, —SO$_2$R, —SO$_3$R in which R is an organic residue.

$R^2$ is preferably the residue of an organoleptic alcohol, phenol or of the enol form of an organoleptic aldehyde or ketone. However, compounds of formula I in which $R^2$ is the residue of a non-organoleptic alcohol, phenol or of the enol form of a non-organoleptic aldehyde or ketone are also useful. $R^2$ contains generally 1 to 30, preferably 1 to 20 C-atoms.

In particular $R^1$ can be alkyl, alkenyl, cycloalkyl, cycloalkenyl, alkylcycloalkyl or aralkyl; $R^2$ hydrogen, alkyl or aralkyl, $R^5$ and/or $R^6$ hydrogen, alkyloxycarbonyl, aryloxycarbonyl, arylalkoxycarbonyl or trialkylsilylalkoxycarbonyl.

Further preferred are compounds of formula I with $R^2$ to $R^7$ being hydrogen.

The compounds of formula I are mostly or nearly odorless at room temperature, atmospheric conditions and about 20 to 100% relative humidity. However, under activating conditions, they are cleaved and one or more active compounds, alcohols, phenols, aldehydes, and/or ketones, optionally with organoleptic and/or antimicrobial properties are generated.

The activating conditions which lead to cleavage of the precursors and thereby to the liberating of the desired active compound(s) may comprise the presence of skin bacteria, especially axilla bacteria, or of an enzyme such as protease or lipase, or elevated temperature or acidic or alkaline pH-values or a combination of two or more of these activating conditions.

In the specific case of usage as alternative substrates, the mechanism may be quite complex. Axillary malodor is generated by certain skin bacteria in the presence of apocrine secretion. Two strains of bacteria which produce axillary malodor when incubated with human apocrine secretions are Staphylococcus and several Coryneform isolates. Production of human axillary malodor can be assayed from these strains of bacteria by incubating cells with apocrine secretions collected from human axilla that has been sterilized in a phosphate buffer at pH 6.8.

The conversion of the naturally occurring apocrine secretion to axillary malodor occurs within the bacterial cells. Extracts of bacteria are capable of converting the apocrine secretion to the malodor compound in an enzymatic process. One of the malodor forming enzymes has been found to be a pyridoxal phosphate dependent amino acid lyase. The enzyme acts to cleave amino acids with the general structure HOOC—CH(NH$_2$)—CH$_2$—XR where X is S or O. The products of the reaction are pyruvate, ammonia, and RXH.

The naturally occurring precursor to axillary malodor in the apocrine secretion is a sulfur containing amino acid. The production of axillary malodor is blocked if an alternative substrate for the malodor forming enzyme is provided, so that the alternative substrate is cleaved instead of the apocrine precursor. The alternative substrates produce either a neutral odor or a pleasant odor upon cleavage.

The presence of alternative substrates (in the axilla) leads to competition with the natural precursor, which is present in low quantities, typically about one nanomole/axilla. Such competition almost completely prevents the malodor precursor from being converted. These compounds therefore serve as deodorants.

It has been surprisingly found that compounds of formula I are useful as alternative substrates competing with the naturally occuring malodor precursors.

Further the compounds of formula I, upon cleavage, provide at least one alcohol, phenol, aldehyde or ketone, all having organoleptic and/or antimicrobial activity and therefore permit the development of useful consumer products with enhanced organoleptic and/or antimicrobial properties. The organoleptic alcohols, phenols, aldehydes, and ketones obtained are useful as fragrances, masking agents and/or antimicrobial agents. Therefore, the invention also relates to the use of all compounds of formula I as precursors for organoleptic compounds, e.g., fragrances, flavors, masking agents, and/or as precursors for antimicrobial agents.

The serine carbonates of formula I can act as precursors in personal care products such as deodorants, in laundry products, cleaning compositions such as all-purpose and hard surface cleaners, pet care products and environment scents such as air fresheners. They can also act as precursors for an odor masking agent and at the same time in the same product as fragrance precursor. They also can act as precursors for antimicrobial agents for these and further products. In deodorants the compounds of formula I act as alternative substrates to the naturally occuring malodor producing enzymes and as precursors for organoleptic and/or antimicrobial substances. The fragrance precursors and the precursors for odor masking agents of the invention may be used individually in an amount effective to enhance or to mask the characteristic odor of a fragrance or a material. More commonly, however, the compounds are mixed with other fragrance components in an amount sufficient to provide the desired odor characteristics. Any person skilled in the art will have knowledge how to make best use of the precursors of the invention.

Due to the in situ generation of the active compounds the desired effect is prolonged and the substantivity of different substrates is enhanced. If two or more active compounds are provided, they can be generated, depending on the precursor and/or the activating conditions, simultaneously or successively. Further, the precursors of the invention provide slow release of the active compounds.

Examples of organoleptic alcohols and phenols include:

amyl alcohol
hexyl alcohol*
2-hexyl alcohol*
heptyl alcohol*
octyl alcohol*
nonyl alcohol*
decyl alcohol*
undecyl alcohol*
lauryl alcohol*
myristic alcohol
3-methyl-but-2-en-1-ol*
3-methyl-1-pentanol
cis-3-hexenol*
cis-4-hexenol*
3,5,5-trimethyl hexanol
3,4,5,6,6-pentamethylheptan-2-ol*
citronellol*
geraniol*
oct-1-en-3-ol
2,5,7-trimethyl-octan-3-ol
2-cis-3,7-dimethyl-2,6-octadien-1-ol
6-ethyl-3-methyl-5-octen-1-ol*
3,7-dimethyl-octa-3,6-di-1-enol*
3,7-dimethyloctanol*
7-methoxy-3,7-dimethyl-octan-2-ol*
cis-6-nonenol*
5-ethyl-2-nonanol
6,8-dimethyl-2-nonanol*
2,2,8-trimethyl-7-nonen-3-ol and 2,2,8-trimethyl-8-nonen-3-ol*
nona-2,6-dien-1-ol
4-methyl-3-decen-5-ol*
dec-9-en-1-ol
benzylalcohol
2-methyl undecanol
10-undecen-1-ol
1-phenyl-ethanol*
2-phenyl-ethanol*
2-methyl-3-phenyl-3-propenol
2-phenyl-propanol*
3-phenyl-propanol*
4-phenyl-2-butanol
2-methyl-5-phenyl-pentanol*
2-methyl-4-phenyl-pentanol*
3-methyl-5-phenyl-pentanol*
2-(2-methylphenyl)-ethanol*
4-(1-methylethyl)-benzenemethanol 4-(4-hydroxyphenyl)butan-2-one*
2-phenoxy-ethanol*
4-(1-methylethyl)-2-hydroxy-1-methyl benzene
2-methoxy-4-methyl phenol
4-methyl-phenol
anisic alcohol*
p-tolyl alcohol*
cinnamic alcohol*
vanillin*
ethyl vanillin*
eugenol*
isoeugenol*
thymol
anethol*
decahydro-2-naphthalenol
borneol*
cedrenol*
farnesol*
fenchyl alcohol*
menthol*
3,7,11-trimethyl-2,6,10-dodecatrien-1-ol
alpha-ionol*
tetrahydro-ionol*
2-(1,1-dimethylethyl)cyclohexanol*
3-(1,1-dimethylethyl)cyclohexanol*
4-(1,1-dimethylethyl)cyclohexanol*
4-isopropyl-cyclohexanol
6,6-dimethyl-bicyclo[3.3.1]hept-2-ene-2-ethanol
6,6-dimethyl-bicyclo[3.1.1]hept-2-ene-methanol*
p-menth-8-en-3-ol*
3,3,5-trimethyl-cyclohexanol
2,4,6-trimethyl-3-cyclohexenyl-methanol*
4-(1-methylethyl)cyclohexyl-methanol*
4-(1,1-dimethylethyl)cyclohexanol
2-(1,1-dimethylethyl)cyclohexanol
2,2,6-trimethyl-alpha-propyl-cyclohexane propanol*
5-(2,2,3-trimethyl-3-cyclopentenyl)-3-methylpentan-2-ol*
3-methyl-5-(2,2,3-trimethylcyclopent-3-en-1-yl)pent-4-en-2-ol*
2-ethyl-4-(2,2,3-trimethylcyclopent-3-en-1-yl)but-2-en-1-ol**
4-(5,5,6-trimethylbicyclo[2.2.1]hept-2-yl)-cyclohexanol*
2-(2-methylpropyl)-4-hydroxy-4-methyl-tetrahydropyran*
2-cyclohexyl-propanol*
2-(1,1-dimethylethyl)-4-methyl-cyclohexanol*
1-(2-tert-butyl-cyclohexyloxy)-2-butanol*
1-(4-isopropyl-cyclohexyl)-ethanol*
2,6-dimethyl-oct-7-en-2-ol**
2,6-dimethyl-heptan-2-ol**
3,7-dimethyl-octa-1,6-dien-3-ol** whereby * indicates the preferred organoleptic alcohols and phenols and ** indicate the more preferred organoleptic alcohols and phenols.
Examples of organoleptic aldehydes include:

2,6,10-trimethylundec-9-enal**
1,2,3,4,5,6,7,8-octahydro-8,8-dimethyl-2-napthalenecarboxaldehyde
2-[4-(1-methylethyl)phenyl]-ethanal
2,4-dimethyl-cyclohex-3-ene-1-carboxaldehyde*
4-carboxaldehyde-1,3,5-trimethyl-cyclohex-1-ene*
1-carboxaldehyde-2,4-dimethyl-cyclohex-3-ene*
1-carboxaldehyde-4-(4-hydroxy-4-methylpentyl)-cyclohex-3-ene*
3,5,5-trimethyl-hexanal
heptanal*
2,6-dimethyl-hept-5-enal**
decanal**
dec-9-enal
dec-4-enal
2-methyldecanal*
undec-10-enal**
undecanal*
dodecanal**
2-methyl-undecanal**
tridecanal
2-tridecenal
octanal**
nonanal*
3,5,5-trimethylhexanal
2-nonenal
undec-9-enal**
2-phenyl-propanal*
4-methyl-phenyl-acetaldehyde*
3,7-dimethyl-octanal*
dihydrofarnesal**
7-hydroxy-3,7-dimethyl-octanal*
2,6-dimethyl-oct-5-enal
2-(4-(1-methylethyl)phenyl)-ethanal*
3-(3-isopropylphenyl)-butanal**
2-(3,7-dimethyoct-6-en-oxy)-ethanal
1-carboxaldehyde-4-(4-methyl-3-penten-1-yl)-cyclohex-3-ene*
2,3,5,5,-tetramethyl-hexanal
longifolic aldehyde
2-methyl-4-(2,6,6-trimethylcyclohex-2-en-1-yl)-butanal*
2-methyl-3-(4-tert-butylphenyl)propanal**
4-(1,1-dimethylethyl)-benzenepropanal*
2-[4-(1-methylethyl)phenyl]-propanal
alpha-methyl-1,3-benzodioxole-5-propanal*
3,7-dimethyl-oct-6-enal*
2-methyl-3-(p-isopropylphenyl)-propionaldehyde**
4-(4-hydroxy-4-methylpentyl)-cyclohex-3-en-1-carboxaldehyde**
alpha-methyl-1,3-benzodioxole-5-propanal*
1-carboxaldehyde-4-(1,1-dimethylethyl)-cyclohexane
4-(octahydro-4,7-methano-5H-inden-5-ylidene)-butanal
[(3,7-dimethyl-6-octenyl)oxy]-acetaldehyde** whereby * indicates the preferred organoleptic aldehydes and ** indicate the more preferred organoleptic aldehydes.
Examples of organoleptic ketones include:

2-heptyl-cyclopentanone
2,2,6,10-tetrametyltricyclo[5.4.0.0(6,10)]-undecan-4-one
benzylacetone*
octan-2-one*
heptan-2-one*
undecan-2-one*
carvone*
1,2,3,5,6,7-hexahydro-1,1,2,3,3,-pentamethyl-4H-inden-4-one*
methyl heptenone*
2,5-dimethyl-oct-2-en-6-one**
2-(butan-2-yl)-cyclohexanone*
2-hexyl-cyclopent-2-en-1-one*
2-(1-methylethyl)-5-methyl-cyclohexanone*
2-(2-methylethyl)-5-methyl-cyclohexanone*
3-methyl-cyclopentadecanone
4-(1,1-dimethylpropyl)-cyclohexanone*
3-oxo-2-pentyl-cyclopentaneacetic acid methyl ester**
1-(1,2,3,4,5,6,7,8-octahydro-2,3,8,8-tetramethyl-2-naphthalenyl)-ethanone*

3-methyl-5-propyl-cyclohex-2-en-1-one*
1-(4-hydroxyphenyl)-butan-3-one whereby * indicates the preferred ketones and ** indicate the more preferred ketone.

Compounds of formula I upon cleavage may also generate antimicrobial compounds. Examples of these compounds are e.g. presented by J. J. Kabara, Cosmet. Sci. Technol. Ser. (16) 1997, p 181–208, especially in Table 8.6.

Of course, the afore mentioned alcohols, phenols, aldehydes, ketones and antimicrobial compounds can serve mutually as fragrances, masking agents and/or antimicrobial compounds. A person of skill in the art is well aware of these interrelationships and can make use thereof to solve a specific problem by using the precursors of the present invention.

It is a matter of course, that it is not possible to give a complete list of the organoleptic and/or antimicrobial alcohols, phenols, aldehydes and ketones which are generated as a result of the desired cleavage of the compounds of formula I by skin bacteria, by enzymes, by elevated temperatures or by acidic and/or alkaline pH-values. The skilled person is, however, quite aware of those alcohols, phenols, aldehydes and ketones which provide the desired organoleptic properties, e.g. for being used as fragrance or for odor masking, and/or showing antimicrobial effects.

The compounds of formula I may preferably be used as sustained release odorants but also to mask or attenuate undesirable odors or to provide additional odors not initially present in consumer products, i.e. personal care products such as cosmetic products, underarm deodorants or antiperspirants or other deodorants contacting the body, or in hand lotions, hair care products such as shampoos and conditioners, baby powders, baby lotions, ointments, foot products, facial cleansers, body wipes, facial makeup, colognes, aftershave lotions, shaving creams, etc. Additional applications include laundry detergents, fabric softeners, fabric softener sheets, (automatic) dishwasher detergents and all-purpose and hard surface cleaners. Further applications are air fresheners and odorants, odor masking agents and/or antimicrobial agents.

The amount required to produce the desired, overall effect varies depending upon the particular compounds of formula I chosen, the product in which it will be used, and the particular effect desired.

For example, depending upon the selection and concentration of the compound chosen, when a compound of the formula I is added either singly or as a mixture, e.g. to a deodorant or laundry product composition at levels ranging from about 0.1 to about 10% by weight, or most preferred about 0.25 to about 4% by weight, an odorant, i.e. one or more odoriferous compounds in an "organoleptically effective amount" is released when the product is used. This newly formed odorant serves to enhance the odor of the product itself or of a fragrance present in the product.

Although deodorancy is the most important concern for the consumer of underarm products, many also choose a product with antiperspirant activity. Current antiperspirant compounds, which are aluminum salts, also function as deodorants by virtue of their germicidal properties.

Thus, if desired, the deodorants of the present invention can be employed with the antiperspirant salts well known in the art. In such formulations, the serine carbonates can be incorporated into a deodorant or antiperspirant formulation along with an antiperspirant salt wherein the antiperspirant salt may be employed in a perspiration reducing effective concentration, e.g., 6 to 30% or in a deodorant effective concentration, e.g., 1 to 6%.

The antiperspirant salt used in the present invention may be any of those which contain aluminum, either alone or in combination with other materials such as zirconium. Typical aluminum salts, although not all-inclusive, include:

aluminum chlorohydrate;
aluminum sesquichlorohydrate;
aluminum dichlorohydrate;
aluminum chlorohydrex PG or PEG;
aluminum sesquichlorohydrex PG or PEG;
aluminum dichlorohydrex PG or PEG;
aluminum zirconium trichlorohydrate;
aluminum zirconium tetrachlorohydrate;
aluminum zirconium tetrachlorohydrex PG or PEG;
aluminum zirconium pentachlorohydrate;
aluminum zirconium octachlorohydrate;
aluminum zirconium trichlorohydrex-gly;
aluminum zirconium tetrachlorohydrex-gly;
aluminum zirconium pentachlorohydrex-gly;
aluminum zirconium octachlorohydrex-gly;
aluminum zirconium chloride;
aluminum zirconium sulfate;
potassium aluminum sulfate;
sodium aluminum chlorohydroxylacetate;
aluminum bromohydrate.

In general, the active antiperspirant salt is present in the same amounts at which such materials are employed in prior art compositions. As a general rule, such compositions contain from about 3% to about 30% preferably from about 10% to about 25%, of the active antiperspirant salt component.

As is evident from the above compilation of alcohols, phenols, aldehydes and ketones, a broad range of known odorants can be generated from precursors of the invention. While manufacturing compositions the precursors of the invention may be used according to methods known to the perfumer, such as e.g. from W. A. Poucher, Perfumes, Cosmetics, Soaps, 2, 7th Edition, Chapman and Hall, London 1974.

Compounds of the formula I can be synthesized in a variety of ways known to those skilled in the art. Convenient methods are outlined in the Examples without limiting the invention thereto.

Compounds of formula I can be prepared by using a wide variety of methods known to the skilled chemist.

For example, for the synthesis of esters see Comprehensive Organic Chemistry, vol. 2, D. Barton, W. D. Ollis, Pergamon Press, p. 871–909

For example, for the synthesis of carbamates see Comprehensive Organic Chemistry, vol. 2, D. Barton, W. D. Ollis, Pergamon Press, p. 1083–1084

For example, for the synthesis of chloroformates see Comprehensive Organic Chemistry, vol. 2, D. Barton, W. D. Ollis, Pergamon Press, p. 1074–1078

For example, for the synthesis of carbonates see Comprehensive Organic Chemistry, vol. 2, D. Barton, W. D. Ollis, Pergamon Press, p. 1070–1072

For example, for the conversion of carbamates to amines and esters to acids see Protective Groups in Organic Synthesis, 2. edition, T. W. Greene, Peter G. M. Wuts, John Wiley & Sons, Inc., 1991

EXAMPLE 1 a) 3-Hydroxy-2-(2-trimethylsilanyl-ethoxycarbonylamino)-propionic acid methyl ester To a mixture of 1.25 g serine methyl ester hydrochloride, 2.25 ml triethylamine and 10 ml dichloromethane was added at 0° C. a solution of 2.22 g carbonic acid 2,5-dioxo-pyrrolidin-1-yl ester 2-trimethylsilanyl-ethyl ester [R. E. Shute, D. H. Rich, *Synthesis*, 1987, 346]. After stirring for 24 h at rt the reaction mixture was washed two times with 1N potassium hydrogen sulfate, once with saturated sodium bicarbonate solution and once with brine. The organic phase was dried over magnesium sulfate, filtered and evaporated to give 2.29 g of a colorless liquid.

$^1$H-NMR (200 MHz, CDCl$_3$): 0.00 (s, 9 H); 0.90–1.02 (m, 2 H); 2.39 (br s, 1 H); 3.77 (s, 3 H); 3.83–4.02 (m, 2 H); 4.35–4.57 (m, 1 H); 5.55 (d, 1 H)

EXAMPLE 2 a) 2-Benzyloxycarbonylamino-3-(1,5,7-trimethyl-octyloxycarbonyloxy)-propionic acid benzyl ester To a mixture of 10 g 2-benzyloxycarbonylamino-3-hydroxy-propionic acid benzyl ester [C. G. Skinner, T. J. McCord, J. M. Ravel, W. Shive, *J. Am. Chem. Soc.*, 78, 1956, 2412] and 10 g 6,8-dimethyl-non-2-yl chloroformate in 80 ml of THF was added a solution of 3.4 ml of pyridine in 40 ml THF at 0° C. The reaction mixture was stirred for 25 h at rt, diluted with ether and washed with 2N hydrochloric acid, saturated sodium bicarbonate and brine. The organic phase was dried and evaporated to dryness. The resulting oil was purified by chromatography on silica gel to yield 14.3 g of a colorless liquid.

$^1$H-NMR (200 MHz, CDCl$_3$): 0.80–1.70 (m, 22 H); 4.35–4.80 (m, 4 H); 5.13 (s, 2 H); 5.20 (s, 2 H); 5.67 (d, 1 H); 7.34 (s, 10 H)

b) 2-Benzyloxycarbonylamino-3-decyloxycarbonyloxy-propionic acid benzyl ester

According to the same procedure 2-benzyloxycarbonylamino-3-decyloxycarbonyloxyl-propionic acid benzyl ester was prepared from 2-benzyloxycarbonylamino-3-hydroxy-propionic acid benzyl ester, decyl chloroformate and pyridine.

c) 2-Benzyloxycarbonylamino-3-phenethyloxycarbonyloxy-propionic acid benzyl ester According to the same procedure 2-benzyloxycarbonylamino-3-phenethyloxycarbonyloxy-propionic acid benzyl ester was prepared from 2-benzyloxycarbonylamino-3-hydroxy-propionic acid benzyl ester, 2-phenyl-ethyl chloroformate and pyridine.

d) 2-Benzyloxycarbonylamino-3-(4-isopropyl-cyclohexyloxycarbonyloxy)-propionic acid benzyl ester According to the same procedure 2-benzyloxycarbonylamino-3-(4-isopropyl-cyclohexyloxycarbonyloxy)-propionic acid benzyl ester was prepared from 2-benzyloxycarbonylamino-3-hydroxy-propionic acid benzyl ester, 4-isopropyl-cyclohex-1-yl chloroformate and pyridine.

e) 2-Benzyloxycarbonylamino-3-dec-9-enyloxycarbonyloxy-propionic acid benzyl ester According to the same procedure 2-benzyloxycarbonylamino-3-dec-9-enyloxycarbonyloxy-propionic acid benzyl ester was prepared from 2-benzyloxycarbonylamino-3-hydroxy-propionic acid benzyl ester, dec-9-enyl chloroformate and pyridine.

f) 2-Benzyloxycarbonylamino-3-(3-methyl-5-phenyl-pentyloxycarbonyloxy)-propionic acid benzyl ester According to the same procedure 2-benzyloxycarbonylamino-3-(3-methyl-5-phenyl-pentyloxycarbonyloxy)-propionic acid benzyl ester was prepared from 2-benzyloxycarbonylamino-3-hydroxy-propionic acid benzyl ester, 3-methyl-5-phenyl-pentyl chloroformate and pyridine.

g) 2-Benzyloxycarbonylamino-3-hex-3-enyloxycarbonyloxy-propionic acid benzyl ester According to the same procedure 2-benzyloxycarbonylamino-3-hex-3-enyloxycarbonyloxy-propionic acid benzyl ester was prepared from 2-benzyloxycarbonylamino-3-hydroxy-propionic acid benzyl ester, hex-3-en-1-yl chloroformate and pyridine.

h) 3-(1,5,7-trimethyl-octylcarbonyloxy)-2-(2-trimethylsilanyl-ethoxycarbonylamino)-propionic acid methyl ester According to the same procedure 3-(1,5,7-trimethyl-octylcarbonyloxy)-2-(2-trimethylsilanyl-ethoxycarbonylamino)-propionic acid methyl ester was prepared from 3-hydroxy-2-(2-trimethylsilanyl-ethoxycarbonylamino)-propionic acid methyl ester, 6,8-dimethyl-non-2-yl chloroformate and pyridine.

i) 2-tert.-Butoxycarbonylamino-3-(1,5,7-trimethyl-octyloxycarbonyloxy)-propionic acid methyl ester According to the same procedure 2-tert.-butoxycarbonylamino-3-(1,5,7-trimethyl-octyloxycarbonyloxy)-propionic acid methyl ester was prepared from 2-tert.-butyloxycarbonylamino-3-hydroxy-propionic acid methyl ester [M. C. Pirrung, S. W. Shuey, *J. Org. Chem.*, 1994, 59, 3890], 6,8-dimethyl-non-2-yl chloroformate and pyridine.

j) 2-Acetylamino-3-(3-methyl-5-phenyl-pentyloxycarbonyloxy)-propionic acid methyl ester According to the same procedure 2-acetylamino-3-(3-methyl-5-phenyl-pentyloxycarbonyloxy)-propionic acid methyl ester was prepared from 2-acetylamino-3-hydroxy-propionic acid methyl ester, [K. Maruyama, M. Hashimoto, H. Tamiaki, *J. Org. Chem.*, 1992, 57, 6143], 3-methyl-5-phenyl-pentyl chloroformate and pyridine.

k) 2-Acetylamino-3-(1,5,7-trimethyl-octyloxycarbonyloxy)-propionic acid methyl ester According to the same procedure 2-acetylamino-3-(1,5,7-trimethyl-octyloxycarbonyloxy)-propionic acid methyl ester was prepared from 2-acetylamino-3-hydroxy-propionic acid methyl ester, 6,8-dimethyl-non-2-yl chloroformate and pyridine.

l) 2-Acetylamino-3-(3,8-dimethyl-oct-6-enyloxycarbonyloxy)-propionic acid methyl ester According to the same procedure 2-acetylamino-3-(3,8-dimethyl-oct-6-enyloxycarbonyloxy)-propionic acid methyl ester was prepared from 2-acetylamino-3-hydroxy-propionic acid methyl ester, 3,7-dimethyl-oct-6-en-1-yl chloroformate and pyridine.

m) 2-Benzyloxycarbonylamino-3-[17-(1,5-dimethyl-hexyl)-10,13-dimethyl-2,3,4,7,8,9,10,11,12,13,14,15,16,17-tetradecahydro-1H-cyclopenta[a]phenantren-3-yloxycarbonyloxy]-propionic acid benzyl ester According to the same procedure 2-benzyloxycarbonylamino-3-[17-(1,5-dimethyl-hexyl)-10,13-dimethyl -2,3,4,7,8,9,10,11,12,13,14,15,16,17-tetradecahydro-1H-cyclopenta[a]phenantren-3-yloxycarbonyloxy]-propionic acid benzyl ester was prepared from 2-benzyloxycarbonylamino-3-hydroxy-propionic acid benzyl ester, 17-(1,6-dimethyl-heptyl)-10,13-dimethyl-hexadecahydro-cyclopenta[a]phenantren-3-yl chloroformate and pyridine.

n) 2-tert.-Butoxycarbonylamino-3-[17-(1,5-dimethyl-hexyl)-10,13-dimethyl-2,3,4,7,8,9,10,11,12,13,14,15,16,17-tetradecahydro-1H-cyclopenta[a]phenantren-3-yloxycarbonyloxy]-propionic acid benzyl ester According to the same procedure 2-tert.-Butoxycarbonylamino-3-[17-(1,5-dimethyl-hexyl)-10,13-dimethyl-2,3,4,7,8,9,10,11,12,13,14,15,16,17-tetradecahydro-1H-cyclopenta[a]phenantren-3-yloxycarbonyloxy]-propionic acid benzyl ester, 17-(1,6- dimethyl-heptyl)-10,13-dimethyl-hexadecahydro-cyclopenta[a]phenantren-3-yl chloroformate and pyridine.

EXAMPLE 3 a) 2-Amino-3-(1,5,7-trimethyl-octyloxycarbonyloxy)-propionic acid

A mixture of 4.81 g 2-benzyloxycarbonylamino-3-(1,5,7-trimethyl-octyloxycarbonyloxy)-propionic acid benzyl ester, 250 ml methanol and a catalytic amount of 10% Pd/C was stirred six hours under an atmosphere of hydrogen. Filtration over Celite and evaporation under reduced pressure gave 2.69 g of colorless crystals.

$^1$H-NMR (200 MHz, CDCl$_3$): 0.80–1.75 (m, 22 H); 3.82–3.90 (m, 1H); 4.35–4.85 (m, 3 H)

b) 2-Amino-3-decyloxycarbonyloxy-propionic acid

According to the same procedure 2-amino-3-decyloxycarbonyloxy-propionic acid was prepared from 2-benzyloxycarbonylamino-3-decyloxycarbonyloxy-propionic acid benzyl ester.

c) 2-Amino-3-phenethyloxycarbonyloxy-propionic acid

According to the same procedure 2-amino-3-phenethyloxycarbonyloxy-propionic acid was prepared from 2-benzyloxycarbonylamino-3-phenethyloxycarbonyloxy-propionic acid benzyl ester.

d) 2-Amino-3-(4-isopropyl-cyclohexyloxycarbonyloxy)-propionic acid

According to the same procedure 2-amino-3-(4-isopropyl-cyclohexyloxycarbonyloxy)-propionic acid was prepared from 2-benzyloxycarbonylamino-3-(4-isopropyl-cyclohexyloxycarbonyloxy)-propionic acid benzyl ester.

e) 2-Amino-3-(3-methyl-5-phenyl-pentyloxycarbonyloxy)-propionic acid

According to the same procedure 2-amino-3-(3-methyl-5-phenyl-pentyloxy-carbonyloxy)-propionic acid was prepared from 2-benzyloxycarbonylamino-3-(3-methyl-5-phenyl-pentyloxycarbonyloxy)-propionic acid benzyl ester.

EXAMPLE 4

2-Amino-3-(1,5,7-trimethyl-octylcarbonyloxy)-propionic acid methyl ester hydro chloride To a solution of 1.42 g 2-tert.-butoxycarbonylamino-3-(1,5,7-trimethyl-octyloxycarbonyloxy)-propionic acid methyl ester in 20 ml of diethyl ether was added 4 ml of an approximately 6.5M HCl/methanol/methyl acetate solution (This solution was prepared by adding 21 g acetylchloride dropwise to 17.5 g methanol, stirring at 0° C. followed by stirring at rt for 2 h.) The mixture was stirred at rt for 30 h. Evaporation of the solvent gave 1.09 g of a colorless oil.

$^1$H-NMR (400 MHz, CDCl$_3$): 0.82–0.90 (m, 6 H); 0.90–1.70 (m, 13 H); 3.86 (s, 3 H); 4.67–4.83 (m, 4 H); 5.68 (br s); 8.81 (br s)

EXAMPLE 5 a) 2-Amino-3-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-propionic acid benzyl ester; compound with trifluoro-acetic acid 2-Amino-3-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-propionic acid benzyl ester trifluoro-acetic acid salt was prepared by treatment of 2-tert.-butoxycarbonylamino-3-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-propionic acid benzyl ester with trifluoric acid to give colorless crystals (mp: 115° C.).

EXAMPLE 6 a) 2-Amino-3-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-propionic acid Extraction of 2-amino-3-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-propionic acid benzyl ester trifluoroacetic acid salt with saturated sodium bicarbonate solution followed by hydrogenation with Pd/C in a mixture of methanol and dioxane afforded 2-amino-3-[17-(1,5-dimethyl-hexyl)-10,13-dimethyl -2,3,4,7,8,9,10,11,12,13, 14,15,16,17-tetradecahydro-1H-cyclopenta[a]phenanthren-3-yloxycarbonyloxy]-propionic acid as colorless crystals (mp: 147° C.).

EXAMPLE 7

To demonstrate the use of compounds of formula I as precursors of fragrances and as alternative substrates for malodor producing enzymes, various derivatives were synthesized and tested for cleavage by *Staphylococcus haemolyticus*, a bacterium commonly found on human skin, especially in the axilla. This example is meant to illustrate, not to limit, the invention.

Assay of the Amino Acid Derivatives for Cleavage by Bacteria

The synthesized amino acid derivatives were tested for their ability to be cleaved by bacteria normally found in human axilla. A 100 ml culture of *Staphylococcus haemolyticus* was grown overnight at 37° C. in TSB medium.

The cells were pelleted by centrifuging the culture at 5,000 rpm for 12 minutes, and the pelleted cells were resuspended in sterile saline. The cells were again pelleted and resuspended in sterile saline. After pelleting the cells once again, the cells were weighed and resuspended in sterile assay buffer (50 mM phosphate, pH 6.8, 1% glucose/dextran). The final concentration of cells was 0.05 g cells/ml (for the gas chromatography (GC) assay). These cell suspensions can be stored at 4° C.

The serine carbonate was prepared as stock solution at a concentration of approximately 5 mg/ml in 50 mM potassium phosphate buffer (pH 6.8). If necessary, the pH can be adjusted to 6.8–7.0 with 1N NaOH. The serine carbonate stock solution was sterilized by filtering through 0.22 μm filters.

Gas Chromatography Assay

To demonstrate that the serine carbonates of the invention can be cleaved by bacteria normally found in axilla, a 100 μl aliquot of a stock solution of the carbonate of Example 3e was added to 100 μl of *Staphylococcus haemolyticus* cells in sterile tubes. For a negative control, the cells were incubated with 100 μl sterile phosphate buffer. To measure spontaneous cleavage of the compound, a blank containing 100 μl of the stock solution in 100 μl sterile phosphate buffer was incubated in the absence of cells. The samples were incubated for 16–18 hours at 37° C., and the reactions were quenched with 10 μl of 10 N HCl. The samples then were extracted into 100 μl chloroform and analyzed by gas chromatography. Data analysis indicated that 140 nmols of 3-methyl-5-phenyl-pentanol was produced by the cell incubation with 350 nmol of the compound from Example 3e indicating that 40% of the precursor was cleaved by the cells.

EXAMPLE 8

Formulations

| | % w/w |
|---|---|
| a) Deodorant Stick | |
| propylene glycol | 70.300 |
| water | 20.500 |
| sodium stearate | 7.000 |
| triclosan | 0.300 |
| fragrance | 1.400 |
| amino acid derivative | 0.50 |
| serine carbonate | |
| total | 100.00 |
| b) Aerosol Antiperspirant | |
| Cyclomethicone (DC-344) | 27.13 |
| aluminum chlorohydrate | 9.65 |
| talc | 2.03 |
| silica | 1.27 |
| amino acid derivative | 1.0 |
| propellant | 58.92 |
| serine carbonate | |
| total | 100.00 |
| c) Solid Antiperspirant Stick | |
| Cyclomethicone (DC-345) | 44.12 |
| aluminum zirconium tetrachlorohydrex-gly | 22.68 |
| Stearyl Alcohol | 15.53 |
| PPG-10 Butanediol | 4.80 |
| $C_{12-15}$ alcohols benzoate | 3.84 |
| Hydrogenated Castor Oil | 2.84 |
| Myristyl myristate | 1.92 |
| PEG-8 distearate | 0.92 |
| Amino acid derivative | 0.50 |
| fragrance | 2.85 |
| serine carbonate | |
| total | 100.00 |
| d) Anydrous Antiperspirant | |
| Cyclomethicone | 74.5 |
| aluminum zirconium tetrachlorohydrex-gly | 20.0 |
| Quaternium 18 Hectorite | 3.5 |
| propylene carbonate | 1.0 |
| amino acid derivative | 1.0 |
| fragrance oil | q.s. |
| serine carbonate | |
| total | 100.00 |
| e) Transparent Antiperspirant Gel | |
| aluminum zirconium tetrachlorohydrex-gly | 23.50 |
| water | 38.75 |
| ethyl alcohol w/20 ppm Bitrex and 0.12% TBA | 9.98 |
| DC 225 fluid | 9.72 |
| propylene glycol | 8.68 |
| Cyclomethicone and Dimethicone copolyol | 8.12 |
| amino acid derivative | 1.0 |
| fragrance | 0.25 |
| serine carbonate | |
| total | 100.00 |
| f) Nonionic O/W, Emollient Cream | |
| silicon latex (DC 2-9065) | 54.54 |
| Dimethicone (DC 225) | 10.00 |
| Cyclomethicone (DC 344) | 6.31 |
| aluminum zirconium tetrachlorohydrex-gly | 25.00 |

-continued

| | % w/w |
|---|---|
| trihydroxystearin | 0.40 |
| hydrated silica (Sylox 2) | 1.00 |
| amino acid derivative | 1.50 |
| fragrance | 1.25 |
| perfume | 0.200 |
| serine carbonate | |
| total | 100.00 |

EXAMPLE 9

Test cloth was washed with a lipase-containing detergent to which one or more of the precursor compounds of Examples 2, 3 and 4 were added. Headspace analysis of the wet and dry laundry indicated the presence of the fragrances derived from the precursor. The fragrance level was higher than when the test cloth was washed with a lipase-containing detergent to which one or more of the corresponding fragrance compounds but no precursor compounds were added.

EXAMPLE 10

Test cloth was washed with a lipase-containing detergent and then a fabric softener, containing one or more of the precursor compounds of Examples 2, 3 and 4 were added to the rinse cycle. Headspace analysis of the wet and dry laundry indicated the presence of the fragrances derived from the precursors. The fragrance level was higher than when the test cloth was washed with a lipase-containing detergent and then a fabric softener, containing one or more of the corresponding fragrance compounds but no precursor compounds, was added to the rinse cycle.

EXAMPLE 11 a) Fabric Softener of the Ester Quat Type Concentrate:

| PHASE A | | |
|---|---|---|
| deionised water | | to 100.0 |
| MgCl$_2$ (saturated sol.) | | 1.0 |
| PHASE B | | |
| REWOQUAT WE 18 | (di-(tallow carboxyethyl) hydroxy ethyl methylammonium methosulfate) | 15.0 |
| GENAPOL O 100 | (ethoxylated fatty alcohol $C_{16}$—$C_{18}$ 10EO) | 2.0 |
| ANTIFOAM DB 31 | | 0.5 |
| PHASE C | | |
| isopropyl alcohol | | 3.0 |
| preservative | | q.s. |
| perfume | | q.s. |

Process

While stirring and heating to 65° C., phase A, phase B preheated to 65° C., were added. After cooling to room temperature, phase C. was added. The pH value of the finished product was 2.60. Delayed precursor compounds of Examples 2,3 and 4 were added either to phase A, B or C in an amount of 1.0% by weight.

b) Fabric softener of the ester quat type concentrate:

| PHASE A | | |
|---|---|---|
| deionised water | | to 100.0 |
| PHASE B | | |
| REWOQUAT WE 18 | (di-(tallow carboxyethyl) hydroxy ethyl methylammonium methosulfate) | 6.0 |
| DOBANOL 25-9 | (ethoxylated fatty alcohol $C_{12}$—$C_{15}$ 9EO) | 0.50 |
| ANTIFOAM DB 31 | | 0.10 |
| PHASE C | | |
| MYACIDE BT 30 | 2-bromo-2-nitropropane 1,3 diol | 0.03 |
| PROXEL GXL | Benzisothiazolinone sodium salt | 0.02 |
| perfume | | q.s. |

Process

While stirring and heating to 65° C., phase A, phase B preheated to 65° C. were added. After cooling to room temperature, phase C. was added. The pH value of the finished product was 3.50. Precursor compounds of Examples 2,3 and 4 were added either to phase A, B or C in an amount of 1,0% by weight.

EXAMPLE 12

The serine carbonate 2-Amino-3-(1,5,7-trimethyl-octyl-oxycarbonyloxy)-propionic acid has been tested in a sniff assay to determine whether, in the presence of *Staphylococcus haemolyticus* and axillary malodor precursors, production of malodor is inhibited and production of fragrance can be detected. For this assay, axillary washes, which contain malodor precursors, were dried into vials at a concentration sufficient to produce a strong axillary malodor when incubated with *Staphylococcus haemolyticus* cells. Vials were incubated at 37° C. with *Staphylococcus haemolyticus* cells. The vials contained either only malodor, or malodor precursors with 0.1% 2-amino-3-(1,5,7-trimethyl-octyl-oxycarbonyloxy)-propionic acid. Control precursor vials were not incubated with the cells. The mixtures were extracted with chloroform and about 10 µl of the chloroform layers were spotted on bibulous paper. After the chloroform had evaporated, the papers were evaluated for malodor level and fragrance level. Evaluations were done by seven judges who rated malodor or fragrance strength on an 8-point scale from 0 (none) to 7 (extremely strong). Results were calculated as percent change from control malodor or precursor fragrance score. Results from this assay are shown below:

Malodor drop 50%

Fragrance increase 30%

These results show that the serine carbonate 2-amino-3-(1,5,7-trimethyl-octyl-oxycarbonyloxy)-propionic acid is cleaved by the cells to produce fragrance and that the decrease in malodor is perceptible.

What is claimed is:

1. A topical deodorant composition comprising a dermatologically acceptable vehicle, an antimicrobial agent and/or an antiperspirant salt, and a serine carbonate compound of the formula:

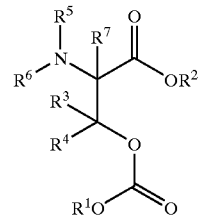

or a salt thereof, wherein $R^1$ is the residue of an organoleptic alcohol, phenol or of the enol form of an organoleptic aldehyde or ketone, $R^2$ is hydrogen, metal, ammonium, straight or branched alkyl, alkenyl, alkynyl, cycloalkyl, cycloalkenyl, heterocycloalkyl, heterocycloalkenyl, aryl, arylalkyl or heteroaryl, whereby all organic residues may contain heteroatoms and/or substituents, $R^3$, $R^4$ and $R^7$ are independently hydrogen or lower alkyl and either $R^3$ and $R^4$ or $R^3$ and $R^7$ or $R^4$ and $R^7$ may form together a ring, and $R^5$ and $R^6$ are independently hydrogen, straight or branched alkyl, alkenyl, alkynyl, cycloalkyl, cycloalkenyl, heterocycloalkyl, an aromatic or heteroaromatic residue, alkylcarbonyl, alkyloxycarbonyl, arylcarbonyl, aryloxycarbonyl, or arylalkyloxycarbonyl and $R^5$ and $R^6$ may together form a ring, whereby all organic residues may contain heteroatoms and/or substituents.

2. The topical deodorant composition of claim 1 wherein the serine carbonate compound is in the form of a quaternary salt.

3. The topical deodorant composition of claim 1 wherein $R^1$ is the residue of an organoleptic alcohol or phenol.

4. The topical deodorant composition of claim 1 wherein $R^2$ is the residue of an organoleptic alcohol, phenol or of the enol form of an organoleptic aldehyde or ketone.

5. The topical deodorant composition of claim 1 wherein $R^1$ is alkyl, alkenyl, cycloalkyl, cycloalkenyl, alkycycloalkyl or arylalkyl, $R^2$ is hydrogen, alkyl or arylalkyl, and $R^5$ and $R^6$ are independently hydrogen, alkyloxycarbonyl, aryloxycarbonyl, arylalkyloxycarbonyl or trialkylsilylalkyloxycarbonyl.

6. The topical deodorant composition of claim 1 wherein $R^2$, $R^3$, $R^4$, $R^5$, $R^6$ and $R^7$ are hydrogen.

7. The topical deodorant composition of claim 1 in the form of a liquid, cream, lotion, gel, stick, aerosol or pump spray.

8. A method of generating a neutral or pleasant odor on human skin which comprises applying to human skin a topical deodorant composition of claim 1.

9. A method of preventing or reducing malodor on human skin which comprises applying to human skin a topical deodorant composition of claim 1.

* * * * *